US012569120B2

(12) United States Patent
Matthison-Hansen et al.

(10) Patent No.: US 12,569,120 B2
(45) Date of Patent: Mar. 10, 2026

(54) ENDOSCOPE

(71) Applicant: AMBU A/S, Ballerup (DK)

(72) Inventors: Kaspar Mat Matthison-Hansen, Helsingør (DK); Thomas Bachgaard Jensen, Værløse (DK)

(73) Assignee: AMBU A/S, Ballerup (DK)

( * ) Notice: Subject to any disclaimer, the term of this patent is extended or adjusted under 35 U.S.C. 154(b) by 491 days.

(21) Appl. No.: 18/100,913

(22) Filed: Jan. 24, 2023

(65) Prior Publication Data

US 2023/0233063 A1    Jul. 27, 2023

(30) Foreign Application Priority Data

Jan. 26, 2022    (EP) ..................................... 22153394
Jan. 19, 2023    (EP) ..................................... 23152474

(51) Int. Cl.
*A61B 1/00*            (2006.01)

(52) U.S. Cl.
CPC ........ *A61B 1/0011* (2013.01); *A61B 1/00045* (2013.01)

(58) Field of Classification Search
CPC .............. A61B 1/00045; A61B 1/0011; A61B 1/00078; A61M 25/0045; A61M 25/0012; A61M 25/0053
See application file for complete search history.

(56) References Cited

U.S. PATENT DOCUMENTS 4,899,787 A    2/1990 Ouchi et al.
4,930,494 A * 6/1990 Takehana ............ F03G 7/06143
                                                         600/145

4,944,287 A    7/1990 Takahashi et al.
5,788,714 A    8/1998 Ouchi
5,810,715 A    9/1998 Moriyama
5,885,207 A    3/1999 Iwasaka
5,885,208 A    3/1999 Moriyama
5,938,587 A    8/1999 Taylor et al.
(Continued)

FOREIGN PATENT DOCUMENTS

EP        1214109 A1    6/2002
EP        1983882 A2    10/2008
(Continued)

OTHER PUBLICATIONS

Anonymous: "Plastics—Thermoplastic materials—Determination of Vicat softening temperature (VST)", International Standard— ISO 306, Ed. 4, vol. 4, No. 306, Jul. 15, 2004, pp. 1-14, XP003031463.
(Continued)

*Primary Examiner* — Monica A Huson

(74) *Attorney, Agent, or Firm* — Faegre Drinker Biddle & Reath LLP

(57)            ABSTRACT

A method for providing an insertion cord of an endoscope with graduated flexibility along the length of the insertion cord. The method includes: providing a main tube having a proximal and a distal end, and subjecting the main tube to a conditioning process including application of heat and a temporary mechanical deformation along at least a part of the length of the main tube between said proximal end and said distal end. The magnitude of the temporary mechanical deformation is varied along said part of the length of the main tube.

18 Claims, 6 Drawing Sheets

(56) References Cited

U.S. PATENT DOCUMENTS

| | | | |
|---|---|---|---|
| 5,976,074 | A | 11/1999 | Moriyama |
| 6,083,152 | A | 7/2000 | Strong |
| 6,203,494 | B1 | 3/2001 | Moriyama |
| 6,206,824 | B1 | 3/2001 | Ohara et al. |
| 6,315,715 | B1 | 11/2001 | Taylor et al. |
| 6,520,214 | B1 | 2/2003 | Sugiyama et al. |
| 6,572,538 | B2 | 6/2003 | Takase |
| 6,579,277 | B1 | 6/2003 | Rabiner et al. |
| 6,860,849 | B2 | 3/2005 | Matsushita et al. |
| 7,169,105 | B2 | 1/2007 | Iwasaka et al. |
| 7,579,550 | B2 | 8/2009 | Dayton et al. |
| 8,075,474 | B2 | 12/2011 | Honda et al. |
| 8,124,876 | B2 | 2/2012 | Dayton et al. |
| 8,246,536 | B2 | 8/2012 | Ochi et al. |
| 8,677,602 | B2 | 3/2014 | Dayton et al. |
| 8,734,695 | B2 | 5/2014 | Yago et al. |
| 8,951,240 | B2 | 2/2015 | Saito et al. |
| 9,044,139 | B2 | 6/2015 | Takahashi |
| 9,839,345 | B2 | 12/2017 | Ueda |
| 10,631,716 | B2 | 4/2020 | Matthison-Hansen |
| 10,645,260 | B2 | 5/2020 | Matthison-Hansen et al. |
| 10,646,107 | B2 | 5/2020 | Matthison-Hansen et al. |
| 10,965,844 | B2 | 3/2021 | Matthison-Hansen et al. |
| 11,337,588 | B2 | 5/2022 | Matthison-Hansen et al. |
| 11,471,029 | B2 | 10/2022 | Morishima |
| 11,478,135 | B2 | 10/2022 | Matthison-Hansen |
| 11,690,502 | B2 | 7/2023 | Matthison-Hansen |
| 2003/0212333 | A1 | 11/2003 | Rabiner et al. |
| 2004/0153049 | A1 | 8/2004 | Hewitt et al. |
| 2004/0186350 | A1 | 9/2004 | Brenneman et al. |
| 2007/0233040 | A1 | 10/2007 | Macnamara et al. |
| 2008/0208001 | A1 | 8/2008 | Hadani |
| 2009/0023989 | A1 | 1/2009 | Honda et al. |
| 2009/0112066 | A1 | 4/2009 | Yago et al. |
| 2009/0312606 | A1 | 12/2009 | Dayton et al. |
| 2009/0318764 | A1 | 12/2009 | Yoshimoto |
| 2010/0076265 | A1 | 3/2010 | Yamakawa et al. |
| 2010/0201029 | A1 | 8/2010 | Yago et al. |
| 2011/0004058 | A1 | 1/2011 | Oneda et al. |
| 2012/0071722 | A1 | 3/2012 | Nakamura et al. |
| 2012/0180896 | A1 | 7/2012 | Takahashi |
| 2012/0273994 | A1 | 11/2012 | Yoshimoto |
| 2013/0046144 | A1 | 2/2013 | Iede |
| 2013/0090632 | A1* | 4/2013 | Tahara .............. A61M 25/0012 |
| | | | 604/526 |
| 2014/0188081 | A1 | 7/2014 | Saito et al. |
| 2014/0303600 | A1 | 10/2014 | Bown et al. |
| 2015/0087905 | A1 | 3/2015 | Ueda |
| 2015/0272424 | A1 | 10/2015 | Abe et al. |
| 2015/0305598 | A1 | 10/2015 | Yamashita |
| 2016/0227982 | A1 | 8/2016 | Takahashi et al. |
| 2017/0010458 | A1 | 1/2017 | Nishijima |
| 2017/0079508 | A1 | 3/2017 | Ikeda |
| 2017/0252536 | A1 | 9/2017 | Yang et al. |
| 2018/0080437 | A1 | 3/2018 | Morishima |

FOREIGN PATENT DOCUMENTS

| | | | |
|---|---|---|---|
| EP | 2052672 | A1 | 4/2009 |
| EP | 2124704 | A1 | 12/2009 |
| EP | 2138089 | A1 | 12/2009 |
| EP | 2215962 | A1 | 8/2010 |
| EP | 2010039 | B1 | 9/2014 |
| EP | 2848187 | A1 | 3/2015 |
| EP | 2853189 | A1 | 4/2015 |
| EP | 2923632 | A1 | 9/2015 |
| EP | 2007463 | B1 | 11/2015 |
| EP | 1987789 | B1 | 6/2016 |
| EP | 2484269 | B1 | 11/2016 |
| KR | 10-2021-0152949 | A | 12/2021 |
| WO | 01/23022 | A1 | 4/2001 |
| WO | 02/69785 | A1 | 9/2002 |
| WO | 2013/027457 | A1 | 2/2013 |
| WO | 2015/029503 | A1 | 3/2015 |
| WO | 2015/198761 | A1 | 12/2015 |

OTHER PUBLICATIONS

ASTM D 1525-00, "Standard Test Method for Vicat Softening Temperature of Plastics", May 1, 2020, ASTM, XP055532247.

European Search Report for EP Patent Application No. 22153394.6, Issued on Jul. 4, 2022, 10 pages.

European Search Report for EP Patent Application No. 23152474.5, Issued on Jul. 25, 2023, 12 pages.

* cited by examiner

ENDOSCOPE

CROSS-REFERENCE TO RELATED APPLICATIONS

This application claims priority from and the benefit of European Patent Application Nos. EP 2215 3394.6, filed Jan. 26, 2022, and EP 2315 2474.5, filed Jan. 19, 2023; said applications being incorporated by reference herein in their entirety.

TECHNICAL FIELD

The present disclosure relates to an endoscope, more specifically to the main tube used in the manufacture of the insertion cord of an insertion endoscope.

BACKGROUND

Insertion endoscopes typically comprise a handle at the proximal end to be gripped by an operator and a flexible elongated insertion cord terminated at the distal end in a tip part at the end of a highly bendable, e.g. articulated, bending section, controllable by the operator. The tip part normally comprises a visual inspection means such as a camera, and illumination means such as LED's or exit apertures of light fibers and whatever optics is needed in that connection. Electrical wiring for the camera and other electronics such as the LED lighting run along the inside of the elongated insertion cord from the handle to the tip at the distal end. When, as mentioned, the illumination is instead fiber-optic, the optical fibers run along inside of the elongated insertion cord.

Thus, the controllable bending section is normally an articulated section at the distal tip of the elongated insertion cord that can be controlled by the operator via control knobs arranged on the handle. Typically, this control is effected by tensioning or slacking pull wires also running along the inside of the elongated insertion cord from the tip part to a control mechanism of the handle. Furthermore, a working channel may run along the inside of the elongated insertion cord from the handle to the tip, e.g. allowing liquid to be removed from the body cavity or allowing the insertion of surgical instruments or the like into the body cavity.

Thus, using the controls allows the operator to advance the distal tip of the endoscope to a desired location by means of a series of actions involving, inter alia, bending the bending section in a desired direction, advancing the elongated insertion cord and turning the elongated insertion cord by turning the handle which is rigidly connected thereto. Navigating a tortuous path of bends and turns to a location of interest may subject the elongated insertion cord including the distal controllable bending section to substantial forces including compression, torsion, and bending. The main body of the elongated insertion cord is essentially only bendable enough to follow the direction taken by the bending section. In fact, it could be said that the purpose of the elongated insertion cord is to transmit the longitudinal pushing forces and rotary torsional forces from the handle to the distal end of the elongated insertion cord in order to allow these maneuvers.

The main body of the insertion cord is typically provided as one single tubular member, or main tube, to a distal end of which the bending section is attached, and where the proximal end is connected to the handle. Accordingly, the main tube must be bendable enough to follow the direction taken by the bending section. This, however, does not imply that the insertion cord and, hence, the main tube must have the same rigidity or bendability along the entire length.

Rather, conversely, for many adaptations of an endoscope to a specific purpose, it is desirable to have a varying or graduated bendability or stiffness along the length of the endoscope insertion cord. Typically, the insertion cord is less bendable at the handle, increasingly more bendable towards the distal end and highly bendable at the bending section.

It is well known to provide the main tube as a composite object comprising multiple layers in the wall forming the main tube. Presuming a generally cylindrical main tube, the main tube would comprise concentric layers, often including a wound coil, a braid surrounding the coil and one or more polymer layers ensuring fluid tightness of the main tube wall. The wound coil and the surrounding braid would typically be made of metal, in particular steel.

An approach to graduating the bendability or stiffness of the main tube is disclosed in U.S. Pat. No. 8,734,695, wherein the outer polymer layer surrounding the coil and braid layers is made of a combination of a soft and a rigid polymer resin. The stiffness along a length of the main tube is varied by varying the ratio of the soft and the rigid resin along the length, e.g. by varying the thickness of respective layers of soft and rigid resin, when extruding them onto the coil and braid layers. This co-extrusion of two layers of varying thicknesses or extruding in two steps, unnecessarily complicates the extrusion process.

Similarly, U.S. Pat. No. 7,169,105 suggests to vary the thickness or material properties of various different layers along the length of the main tube in order to achieve a graduated bendability or stiffness along the length thereof.

BRIEF DESCRIPTION OF THE DISCLOSURE

On this background it is the object of the present disclosure to provide, in a cost-efficient manner, a main tube with graduated bendability for the insertion cord of an endoscope, in particular a disposable i.e. single-use, endoscope that is to be disposed of after use in a procedure on one single patient, rather than being cleaned, disinfected, sterilized etc. and re-used in a new procedure on another patient.

According to a first aspect of the disclosure this object is achieved by a method for making an insertion cord of an endoscope, the method comprising heating a portion of a main tube comprising a metal core and a polymer material surrounding the metal core, said heating placing the polymer material in a softened state, and bending the portion of the main tube while the polymer material is in the softened state. The heating and bending may be referred to as the "conditioning process."

Subjecting the main tube for the insertion cord to this kind of mechanical and thermal conditioning has been found to influence the bendability of the insertion cord in the desired manner. This conditioning has furthermore been found to persist at least for the necessary duration of the single use of a disposable endoscope. There may be some recovery by the main tube but this may easily be compensated during the conditioning process.

In a variation of the present embodiment, the method further comprises unbending the portion of the main tube. Unbending the portion of the main tube comprises bending the main tube at an angle opposite the bending angle and may be referred to as counter-bending the main tube. In one example of the present variation, the method further comprises, after unbending the portion of the main tube, bending and unbending the portion of the main tube a second time. Said bending and unbending may be complementary. The total amount of bending and unbending should match to return the main tube to its original, straight, state. In FIGS. 5A to 5C bending is performed by the guiding wheel preceding the push-wheel. The push-wheel unbends (bends the main tube in the opposite way) on the first 90 degree arc of contact with the main tube and bends on the second 90 degree arc of contact. The second unbending is performed by the guiding wheel following the push-wheel.

The bending, unbending, and optionally bending/unbending the second time may be continuous. Continuous bending and unbending may be achieved by pulling or pushing the main tube over arcuate supports that bend and/or unbend the main tube as the main tube translates over the arcuate supports. The arcuate supports may comprise surfaces of transverse bars, pulleys, slotted wheels, and any other support with a curved surface.

In one example of the present variation, the polymer material has a first temperature when the portion of the main tube is bent and a second temperature, lower than the first, when the portion of the main tube is unbent. Optionally, the polymer material has a third temperature when the portion of the main tube is bent the second time. The third temperature may be lower than the second temperature. The polymer material has a fourth temperature when the portion of the main tube is unbent the second time. These temperatures can be achieved by only heating the polymer material before bending the portion of the main tube being conditioned. Because the unbending occurs after the bending, a certain amount of time passes between the bending and the unbending, and during that time the polymer material cools, reducing its temperature from the first temperature to the second temperature. Preferably the heating is up to but not exceeding the melting point of the polymer material. The high heating temperature will maintain the polymer material in the softened state longer than heating at a lesser temperature. Additional heating may be applied to extend the time that the polymer material on the portion of the main tube being conditioned remains in a softened state. The additional heating should not, however, negate the conditioning effect already imparted onto the main tube.

In an additional example of the present variation, which is preferably combined with the previous example, the main tube is rotated and conditioned again after the rotation. The rotation of the main tube may comprise at least 70 degrees, preferably 80 degrees, and even more preferably at least 90 degrees. Rotation and reconditioning of the main tube imparts graduated flexibility on a different plane from the first conditioning.

In any of the variations and examples of the method according to the first aspect, the main tube may comprise a braid between the metal core and the polymer material. The braid may comprise metal.

In any of the variations and examples of the method according to the first aspect, the polymer material may comprise a single polymer layer or more than one layer. Two or more layers may be co-extruded onto the metal core or the braid.

In any of the variations and examples of the method according to the first aspect, the heating may be inductive or conductive. Heating the metal core has the added advantage of maintaining the polymer material in the softened state for a longer period of time due to more energy being retained in the metal core than in the polymer material and the energy then transferring to the polymer material.

In one variation of the present embodiment, subjecting the main tube to the conditioning process comprises applying heat and a temporary mechanical deformation along at least a part of the length of the main tube between a proximal end and a distal end thereof, wherein the application of heat raises the temperature of the polymer material to soften the polymer material. The magnitude of the temporary mechanical deformation may be varied along the part of the length of the main tube. The polymer material may be heated, for example, to a temperature above half the Vicat temperature but below the melting point of the polymer material.

According to an embodiment of the first aspect of the disclosure, the method comprises providing a main tube as a composite object comprising multiple layers, said multiple layers comprising at least one metal layer and a polymer material, and said main tube having a proximal and a distal end, subjecting the main tube to a conditioning process comprising application of heat and a temporary mechanical deformation along at least a part of the length of the main tube between said proximal end and said distal end, wherein the application of heat raises the temperature of the polymer material to a temperature above the Vicat temperature of the polymer material but below the melting point of the polymer material, and wherein the magnitude of the temporary mechanical deformation is varied along said part of the length of the main tube.

In any of the embodiments, variations and examples of the method according to the first aspect, the heat may be applied locally to the main tube so as to increase the temperature of a sector or section of the main tube during the temporary mechanical deformation of that sector. This has been found to suffice to influence the bendability of the main tube in conjunction with the mechanical deformation.

In any of the embodiments, variations and examples of the method according to the first aspect, the heating is adjusted to raise the average temperature of the polymer material at the temporary mechanical deformation to at least the Vicat softening temperature of the polymer material. This has been found to further improve the conditioning of the main tube.

In one variation of the present embodiment, the heating is adjusted to raise the average temperature of the polymer material at the temporary mechanical deformation to a temperature above the Vicat temperature but below the melting point of the polymer material. Experiments have shown that using a temperature just below the melting point of the polymer and therefore above the vicat softening point, is efficient in achieving a high effect of the graduation. This has thus been found to even further improve the conditioning of the main tube.

Accordingly, in any of the embodiments, variations and examples of the method according to the first aspect, the heating may be adjusted to raise the average temperature of the polymer material positioned before the temporary mechanical deformation to a temperature above 90% of the melting temperature, preferably above 95% of the melting temperature of the polymer material. This has been found to achieve even better the desired conditioning and bending properties of the main tube.

According to a further embodiment of the first aspect of the disclosure, the temporary mechanical deformation comprises a meander bend in a transverse direction of the main tube. Using a meander bend essentially bends the main tube twice, one 180° bend in one direction and two 90° bends in the opposite direction, that is to say in the order: 90°-180°-90°. These angles need not necessarily be very accurate and it can easily be envisaged that they will deviate, especially when the deflection in the mechanical condition is very small. In any case, it is the intention that the bends thus compensate each other and ensures that the main tube remains straight after the conditioning process.

According to a variation of the present embodiment, the size of the meander bend in the transverse direction of the main tube increases linearly along said part of the length of the main tube from the proximal end towards the distal end of the main tube. This advantageously imparts the main tube with a bendability that increases in a similar, i.e. more of less linear, manner towards the distal end along said part of the length of the main tube conditioned in the process. At the proximal end the transition from initial stiffness to gradually increasing bendability is less of a problem, as this part is less likely to enter the patient. It is also often desirable that only a minor part of the length of the tube is conditioned. In any case, also at the proximal end the unconditioned part could be cut away. Increasing the size of the meander bend means, in the present context, that the distance between the first and last bend increases. Without being bound by theory, it is believed that the increased size increases the cooling time between the first bend (shortly after the heater) and the last bend (furthest away from the heater), and thus the cooling time increases a temperature differential of the portion of the main tube between the first and the last bent, the increased temperature differential resulting in greater flexibility. As discussed below, a piston can be used to increase the size of the meander bend, whereby movement of the piston increases the resulting flexibility proportionally to the distance of travel of the piston.

Accordingly, in some embodiments the part of the length subjected to the conditioning process is at least 15%, preferably at least 25%, and more preferably at least 35% of the length of the main tube between the proximal end and the distal end. The length will, inter alia, depend on the purpose and the nature of the endoscope in which the conditioned main tube is implemented.

In any of the embodiments, variations and examples of the method according to the first aspect, the main tube comprises steel parts and the heat is applied to the steel parts by electromagnetic induction. This has been found to be a very efficient heating method, which moreover is readily applicable as steel parts such as coils and braids are usually present in main tubes anyway.

According to a further embodiment of the invention, a ceramic heating element is used to irradiate heat towards the main tube. This provides heating irrespective of the magnetic properties of the composite main tube.

According to an embodiment of the first aspect of the disclosure, the main tube is subjected to the conditioning process twice, in particular the main tube is rotated 90° before being subjected to the conditioning process the second time. This 90° rotation need not be very accurately obtained. The main issue is that the conditioning is performed in different directions, and anything in the interval between 70° and 130° would suffice. This imparts the graduated bendability to the main tube in several cross-wise directions, i.e. so that the graduated bendability is not only present in a left-right direction but also in an up-down direction, when looking at a horizontally orientated bending section.

According to a second aspect of the disclosure, the object is also achieved by an endoscope comprising a main tube conditioned using a process according to the first aspect of the disclosure.

According to a third aspect of the disclosure the object is also achieved by a system comprising a display device, and an endoscope according to the second aspect of the disclosure adapted to be connected to the display device.

BRIEF DESCRIPTION OF THE DRAWINGS

The present disclosure will now be made in greater detail based on non-limiting exemplary embodiment and with reference to the drawings, in which.

DETAILED DESCRIPTION

Figures 1, 2:
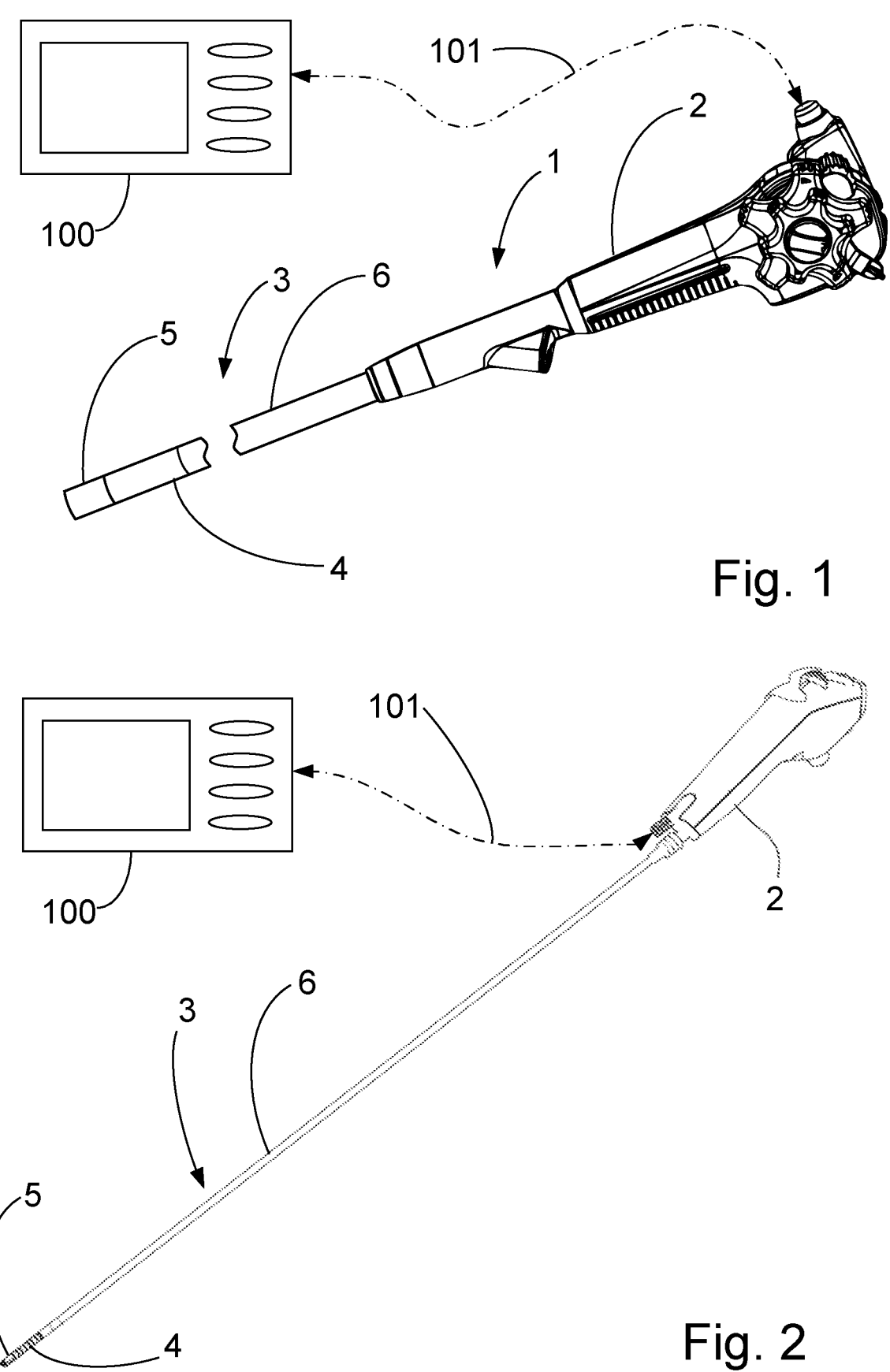
FIG. 1 shows a first system comprising a display unit and a first endoscope according to the disclosure connected to the display unit.
FIG. 2 shows a second system comprising the display unit and a second endoscope according to the disclosure connected to the display unit.

Turning first to FIG. 1, a system comprising an endoscope 1 connectable to a display unit 100 via a cable 101, or other communication means such as wireless communication, is shown. Endoscopes include procedure-specialized endoscopes, for example bronchoscopes, arthroscopes, cystoscopes, ureteroscopes, cholangioscopes, colonoscopes, laparoscopes, gastroscopes, and duodenoscopes. The endoscope 1 shown in FIG. 1 is a duodenoscope. A similar system comprising a different type of endoscope 1, such as a bronchoscope, connectable to a display unit 100, is shown in FIG. 2. The endoscopes 1 are disposable, meaning that they are disposed after use in a single patient and not sterilized or stored for subsequent use, even with the same patient. The display unit 100 can be used multiple times and could be the very same device in FIGS. 1 and 2.

The endoscope 1 comprises a handle 2 and an insertion cord 3 extending from the distal end of the handle. At the distal end the insertion cord 3 terminates in a bending section 4 with a tip housing 5. The insertion cord 3 furthermore comprises a main tube 6, which, in accordance with the disclosure, has been conditioned to achieve a graduated bendability, preferably a bendability that increases along the length of the insertion cord 3 from the handle towards the bending section 4. In FIG. 1 the insertion cord 3 has been shortened for illustration purposes. The insertion cords for duodenoscopes and colonoscopes may be more than a meter long, e.g. 1,250 mm or 1,500 mm. The colonoscope may be 12 mm in diameter. The insertion cords of bronchoscopes are shorter and thinner.

Examination of human cavities with the endoscope 1 may be carried out to determine whether a patient has disease, a tumor, an infection, or the like, and in some cases samples may be taken/removed from the human cavity. For instance, bronchoscopies or colonoscopies may be carried out to examine whether a patient has a lung or colon disease, respectively, a tumour, or the like. The endoscope 1 comprises an image sensor, such as a camera, in the tip housing 5 and connected to the display unit 100 so as to provide the medical personnel with a view of the part of the patient's body being examined. The handle 2 has a steering control lever for manoeuvering the tip housing 5 by means of a steering wire or wires.

In assembling the endoscope 1, the bending section 4 is connected to the distal end of the main tube 6 and the proximal end of the main tube 6 is connected to the distal end of the handle 2. A section of a typical main tube 6 is shown in cross-section in FIG. 6 with layers partially removed for illustration purposes. A typical main tube 6 that could be used in this disclosure will comprise at least an inner wound coil member 23, preferably made of steel. The inner wound coil member 23 is surrounded by a braid 22, preferably also made of steel. The braid 22 (and the wound coil member), in turn, is covered by a fluid tight layer which is typically extruded onto the coil member 23 and braid 22 assembly. The extruded fluid tight layer is typically a polymer layer 24. The extruded fluid tight layer 24 may comprise a single layer or several polymer layers. Multiple polymer layers may be provided individually or may be provided in a co-extruded multilayer structure. For example, the skin layer of the multilayer polymer layer may provide strength or puncture resistance while an inner layer may be tailored to bond to the braid 22 or to the coil member 23 if a braid 22 is not used. An intermediate layer may be provided to compatibilize the skin and inner layers. The skin layer may also include lubricious additives to facilitate extrusion or navigation of the insertion cord in the patient.

The main tube 8 is subjected to a conditioning treatment in accordance with the present disclosure to provide the desired varying or graduated bendability. The conditioning treatment can be applied to the main tube before or after assembly of the endoscope and before or after attachment of the bending section ot the main tube. The conditioning treatment is preferably applied before the main tube is attached to the handle. The graduated bendability can comprise two or more sections with different flexibility, where the flexibility within each section is substantially constant. The graduated bendability can also comprise two or more sections with different flexibility, where the flexibility within at least one of the sections varies, potentially in a continuous manner.

Figure 3:
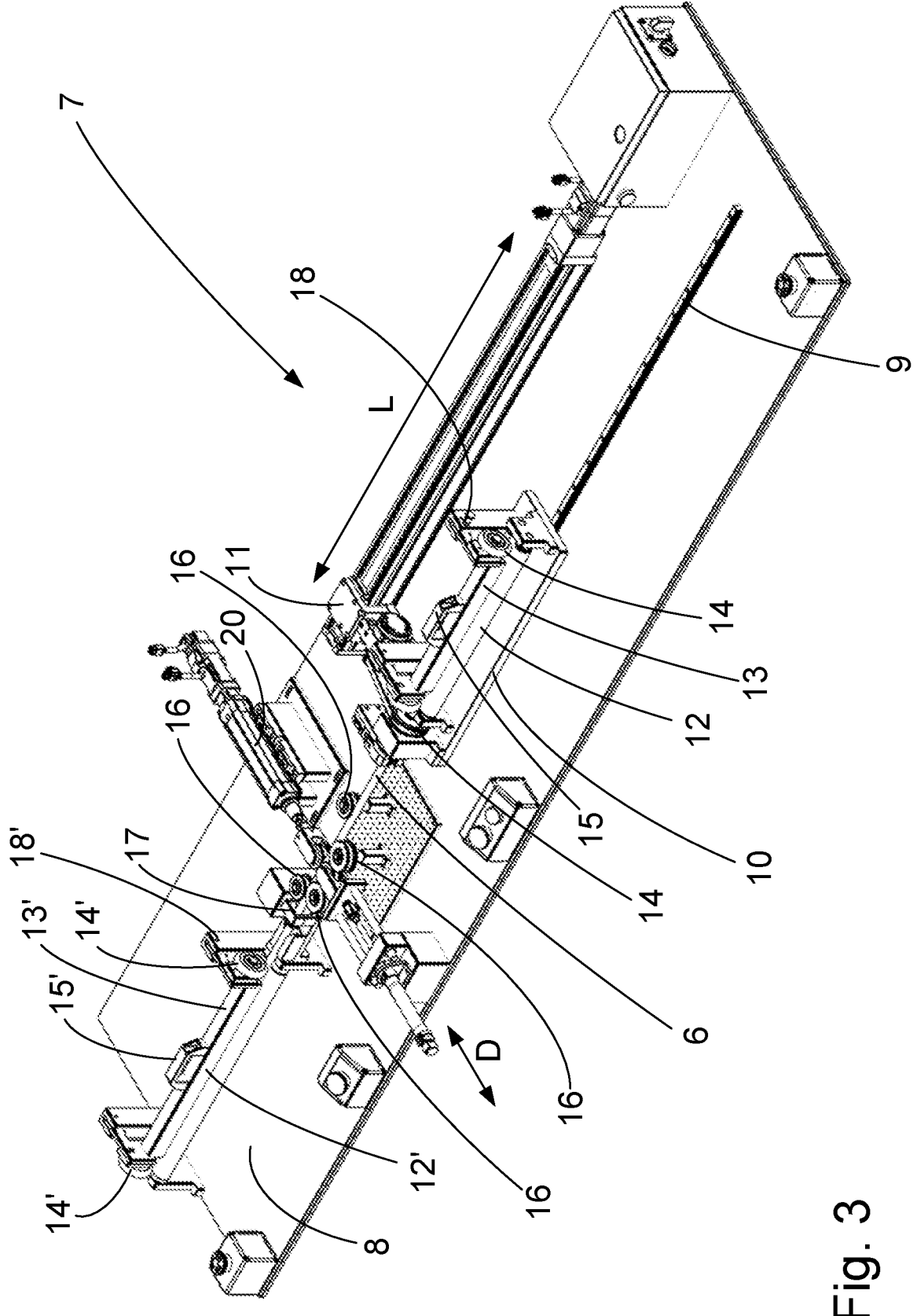
FIG. 3 shows an isometric view of a conditioning apparatus adapted to condition the main tube for an endoscope in accordance with the disclosure.
Figure 4:
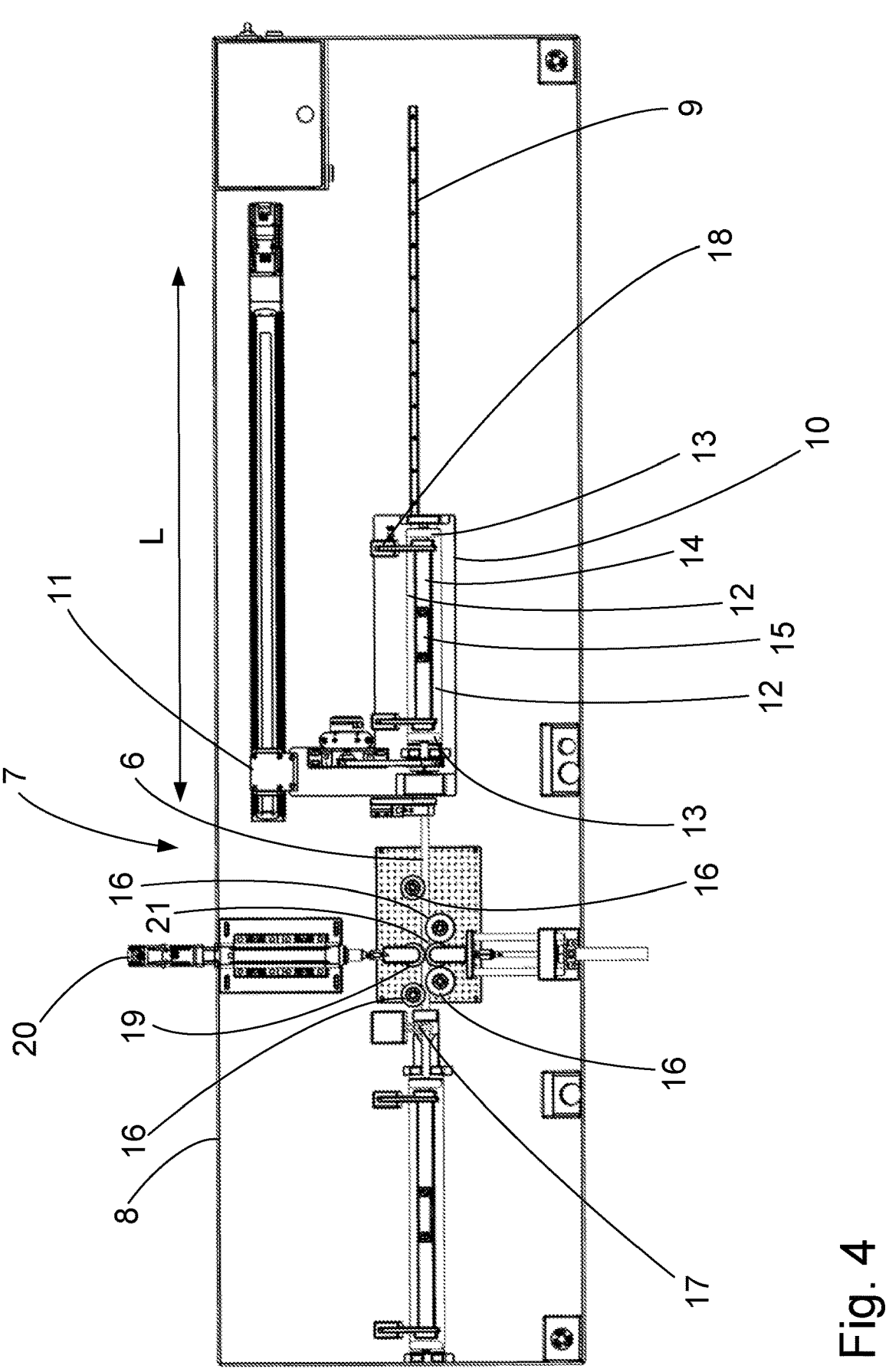
FIG. 4 shows a top plan view of the conditioning apparatus according the FIG. 3.

FIGS. 3 and 4 show a main tube 6 placed in a conditioning apparatus 7 adapted to be used in the conditioning according to the disclosure. As will be understood from the description below, the depicted situation is an initial position just before the start of a conditioning run.

In the depicted embodiment the conditioning apparatus 7 comprises a base plate 8, e.g. a table top, a work bench or the like, or a separate base plate 8 to be placed on one of the former. An elongate guide means, or guide, such as a groove in the base plate 8 or a rail 9 provided thereon is provided to guide a sled member, or sled, 10 during a reciprocating movement indicated by the double arrow L. The reciprocation movement may be effected by a suitable actuator 11, such as a linear actuator. The linear actuator could comprise a linear threaded rod rotated by a gear of an electric motor to effect linear translation. The motor could be a servo motor, a stepper motor, or any motor in which the rotation speed can be controlled by a motor drive. The linear actuator can also be a pneumatic or hydraulic actuator or any other suitable actuator allowing a controlled reciprocating movement of the sled member 10. Pneumatic and hydraulic actuators are operated by controlled fluid pressure, as is known in the art.

The sled 10 comprises a pair of rollers 12 on which the main tube 6 is placed during the conditioning and held down by a guide 13 having a pair of wheels 14 arranged at either end. The guide 13 may comprise additional weight to hold down the main tube 6. To allow the placement of the main tube 6, the guide 13 is arranged on a pair of pivots 18 or hinges, so that it may be swung out of the way using a handle 15.

When the guide 13 is swung out of the way, the main tube may be placed with the part later to constitute the proximal end on the rollers 12 and with the distal end extending from the sled and between a set of guiding pulley wheels 16 or the like forming part of a bending mechanism. The most proximal portion of the main tube 6 that is to be conditioned is placed in close proximity to a heating member 17. In the currently preferred embodiment of the conditioning apparatus the heating member is an induction coil surrounding the main tube and allowing the steel therein to be heated by electrical current provided to the induction coil. Evidently, other heating means may or must be used, e.g. if the main tube 6 does not include steel or other material suitable for induction heating. Irradiation with heat from one or more ceramic heating elements arranged suitably around the main tube may be used. Even main tubes without metals, e.g. non-metallic braids or coils, may also be conditioned using the method according to the present disclosure.

For proper holding of the main tube 6, a stationary arrangement corresponding that on the sled 10 may be arranged on the other side of the pulley-wheels 16, e.g. comprising a pair of rollers 12' on which the main tube 6 is placed during the conditioning and held down by a guide 13' having a pair of wheels 14' arranged at either end. This guide 13' may also incorporate additional weight to hold down the guide 13' and the main tube 6. To allow the placement of the main tube 6, the guide 13' is likewise arranged on a pair of pivots 18' or hinges, so that it may be swung out of the way using a handle 15'.

In conjunction with the set of guiding wheels 16 the bending mechanism comprises a push-wheel 19 arranged in conjunction with a second linear actuator 20 arranged to displace the push-wheel 19 in a transverse direction, i.e. cross-wise to the reciprocating movement of the main tube 6 on the sled 10 but in the same (horizontal) plane, i.e. in a plane parallel to the base plate 8. This allows a transverse force to be applied locally to the main tube 6. A slave wheel 21 or other follower may be arranged opposite the push-wheel 19 on the other side of the main tube 6 and biased against the push-wheel 19 so as to hold and guide the main tube 6 under the pressure of the second actuator 20 and the push-wheel 19.

Figures 5A, 5B:
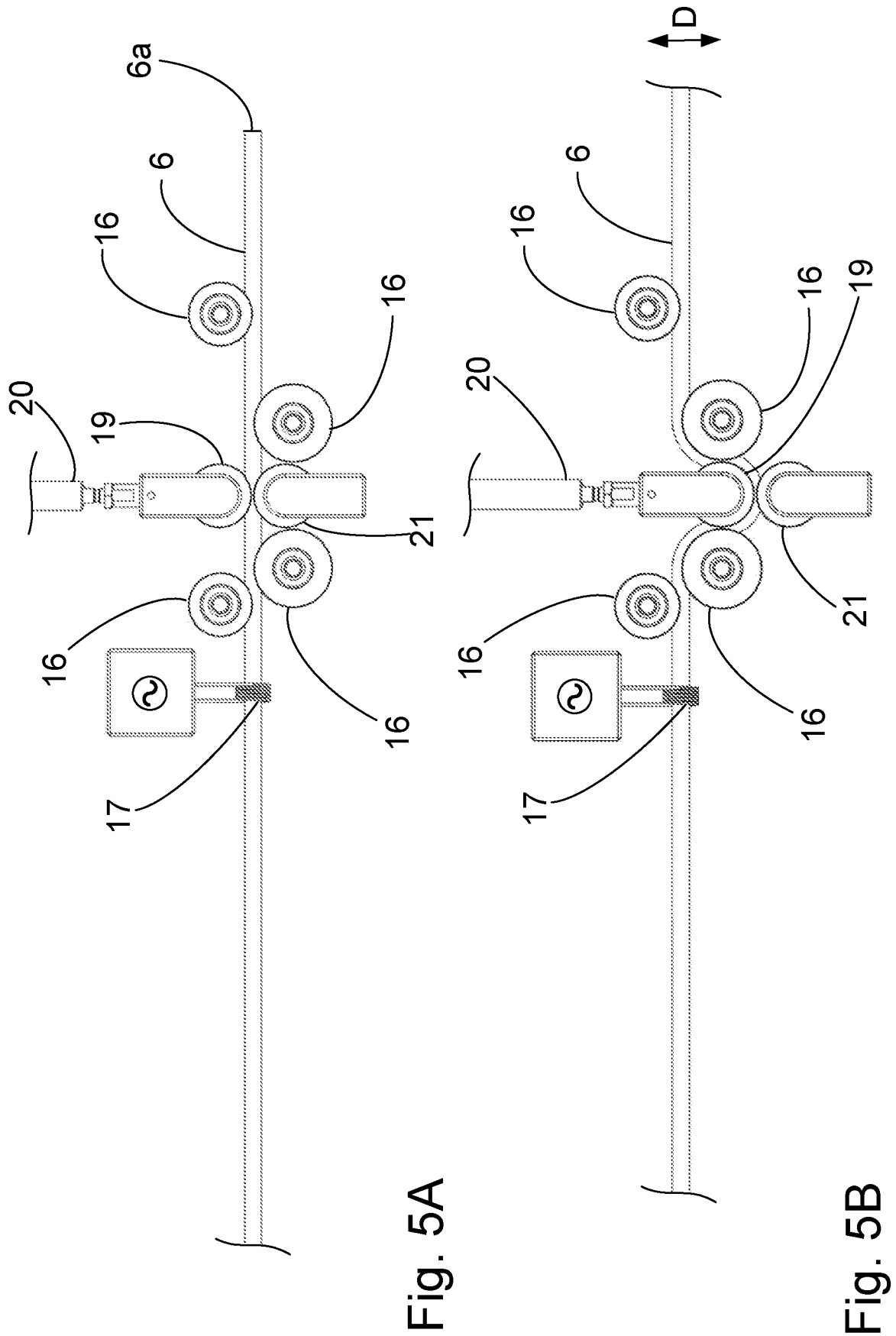
FIGS. 5A-5C shows details of the conditioning apparatus with the main tube in various stages of the conditioning process.
Figure 5C:
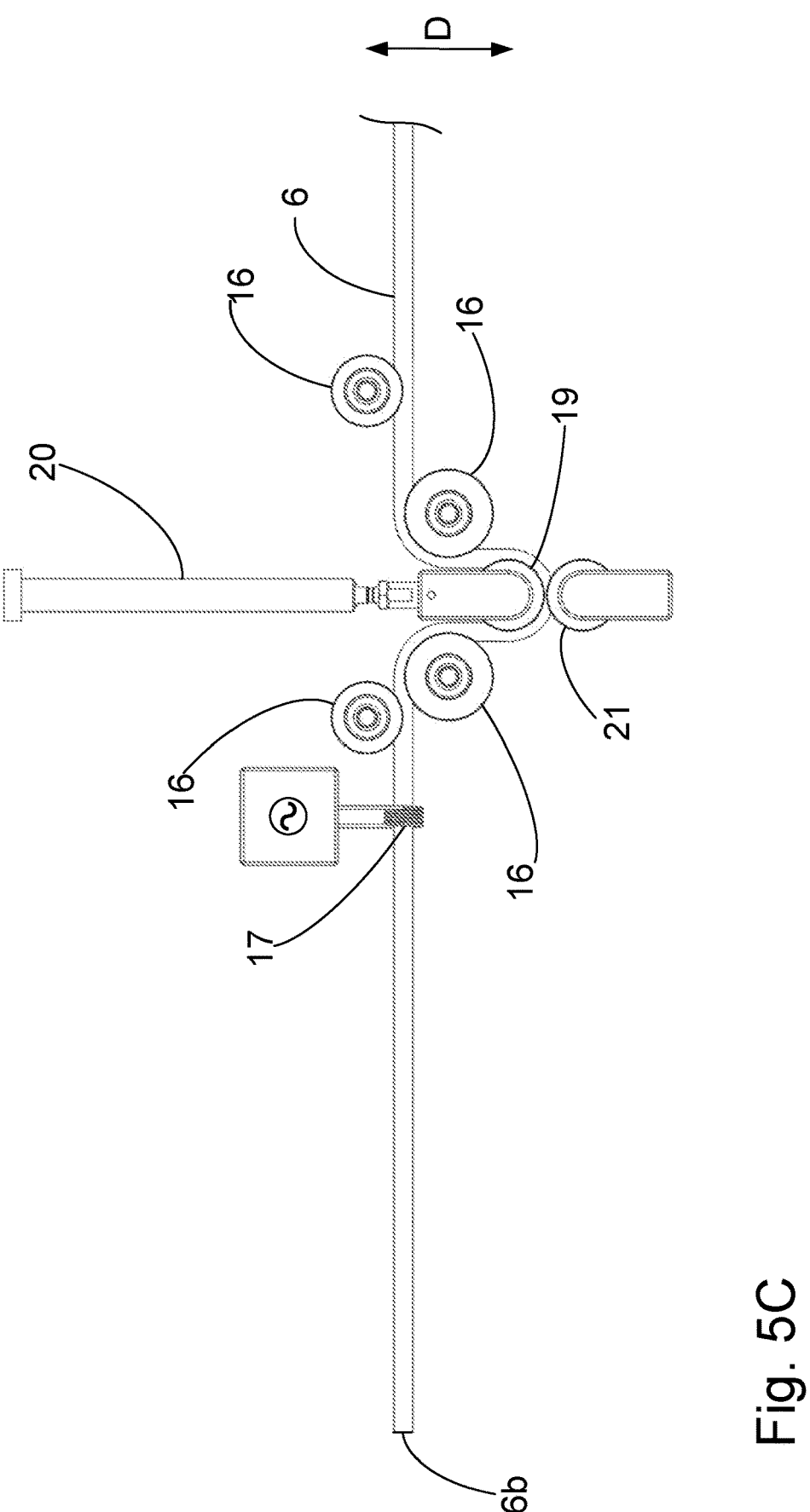

The process of conditioning a main tube 6 using the conditioning apparatus 7 will now be described in conjunction with FIGS. 5A-5C showing the bending mechanism in greater detail.

Figure 6:
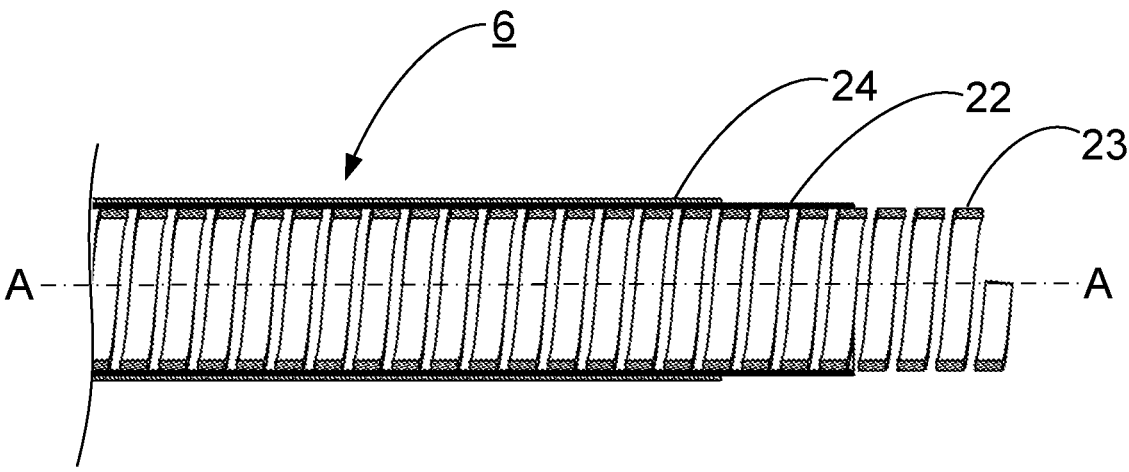
FIG. 6 shows a cross-section of a section of a main tube applicable in the present disclosure.

In FIG. 5A a main tube 6 has been passed through an induction coil providing the heating member 17 and between the pulley-wheels 16 as well as the push-wheel 19 and the slave wheel 21. No force or heating is applied to the main tube 6 yet and it is therefore in the straight as-made condition, i.e. cylindrical around a longitudinal axis A-A, as shown in FIG. 6. The proximal end 6a of the main tube 6 at the right-hand side of FIG. 5A is located and held on the sled 10 (shown in FIGS. 3 and 4). In FIG. 5C the distal end 6b of the main tube 6 is seen on the left-hand side.

When the conditioning starts, alternating current is supplied to the induction coil which generates eddy currents in the steel parts of the main tube 6, such as the braid 22 or the coil 23, cf. FIG. 6. This, in turn, heats up the outer polymer layer 24 covering the braid 22. At the same time the sled 10 starts pulling the main tube 6 though the induction coil of the heating member 17 towards the right-hand side of FIG. 5A, so that heating will be applied locally over a short length of the main tube 6 as it is moved through the induction coil of the heating member 17. In this respect it should be noted that the use of an induction coil is only one way of heating, irradiation or heat transfer from a heated fluid could also be used.

As the first actuator 11 pulls the sled 10 and thus the main tube 6 to the right-hand side in FIGS. 5A-5C, the second actuator 20 moves the push-wheel 19 in a cross-wise direction, as indicated with the double arrow D, to bend the main tube around the push-wheel 19 and at least some of the pulley-wheels 16, preferably in a meander bend as shown in FIGS. 5B and 5C. This happens while the local heating of the main tube 6 is still present, so that the meander bend of the main tube 6 is hot. The most proximal portion of the main tube 6 that is to be conditioned reaches the push-wheel 19 first, with other portions following. As the push-wheel 19 translates further, the amount of conditioning increases. If the push-wheel 19 translates in a continuous manner, whether at a constant or variable speed, the conditioning will also be continuous albeit graduated or variable based on the movement of the push-wheel 19.

By comparison between FIGS. 5B and 5C it can be understood that for this embodiment the stroke of the second actuator 20 increases while the main tube 6 is pulled through the pulley-wheels 16 so that the size of the meander bend imparted to the main tube 6 increases towards the distal end of the main tube 6. This continues until eventually the distal end reaches the pulley-wheels 16. At this stage it is preferred to stop the pulling of the main tube 6, stop supplying current to the heating member, and return the push-wheel 19 to the original neutral position, i.e. as shown in FIG. 5A.

The lateral deflection need not be performed as a smooth sliding motion by the actuator 20. Embodiments where the conditioning process is applied more step-wise are also part of the disclosure. E.g. the actuator 20 could maintain the same stroke to give the same deflection for one section of the length of the main tube 6 being conditioned, then the actuator 20 is moved momentarily to a new stroke where another sector of the length of the main tube 6 is conditioned and so on.

The speed at which the main tube 6 passes through or by the heating member 17 can also be varied. In one variation of the present embodiment, the main tube 6 is translated by the sled at a speed that decreases from an initial speed. In one example, the speed decreases at a rate of about 1 mm/sec. The initial speed may be about 15 mm/sec. In another example, the speed decreases at a first rate for a portion to be conditioned, then the speed decreases at a second, faster, rate for the next portion to be conditioned, and finally the speed increases at a third rate for a third portion to be conditioned. The absolute magnitude of the second and third rates might be the same. The second rate may be 2-3 times the first rate. In one specific example, the first rate is about-1 mm/sec, indicating a speed decrease, the second rate is about-2.5 mm/sec, and the third rate is 2.5 mm/sec. The first portion maybe 20 cm long, the second portion may be 20 cm long, and the third portion may be 30 cm long. Of course the portions could have the same length or different lengths. The transition from one rate to the next is, preferably, made gradually.

The distance from the heating member 17 to the center of the push-wheel 19 when the center of the push-wheel 19 is aligned with the main-tube 6/heating member 17 can be between 60 and 120 mm, preferably between 80 and 110 mm. The smaller end of the range is to account for the diameter of the wheel 16 between the heating member 17 and the push-wheel 19 and also the diameter of the push-wheel 19. The wheels 16 that bend/unbend the main tube 6 may comprise inner diameters of about 35-60 mm, preferably between about 40-50 mm. The push-wheel 19 may comprise an inner diameter of about 25-50 mm, preferably between about 30-40 mm. The push-wheel 19 may travel in the order of 40 mm to create the meander bend. Of course these values are one example for one type of tube and are demonstrated to condition the main tube 6 without damaging or causing permanent deformation of the core of the main tube 6, which in this case may be in the range of 8-16 mm in diameter.

With the push-wheel in the neutral position the first actuator 11 may push the sled 10 and the main tube back to the original position.

From here the wheels 13 and/or the rollers 12 may be used to rotate the main tube 6 by 90°, upon which the process of propagating the meander bend as a wave along the main tube 6 described above may be repeated to achieve a conditioning in the orthogonal direction. The rotation by 90° could of course also be achieved by other means, e.g. by gripping and turning the main tube manually. Further conditioning, e.g. turning a further 90° (twice) to effect conditioning in the opposite directions has been found not to be necessary, but would of course be possible, as would angles in between.

Rather than controlling the push-wheel 19 using an electrical, pneumatic or hydraulic linear actuator, the push-wheel 19 could be moved mechanically. That is to say, be part of a cam follower in the bending mechanism. The cam itself would extend along the main tube 6 in a fixed relation thereto, allowing a linear motion of the bending mechanism along the length of the main tube 6 to be converted into a lateral pushing motion dependent on the shape of the cam. A straight wedge-shaped cam would thus provide a constant linear increase in deflection, when moving the bending section along the main tube 6. A cam with a specific curvature could also be used to impart specific bending properties. Needless to say that the electrical, pneumatic or hydraulic linear actuator could also be controlled in a non-linear manner to impart specific bending properties. The skilled person will be able to devise many different setups to achieve the mechanical conditioning, including multiple meanders, and coiling i.e. bends of more than 360°, without departing from the disclosure and the scope of the claims.

The maximum degree of mechanical deflection imparted will depend on the dimensions of the main tube, i.e. diameter and overall length as well as the procedures the endoscope is designed for.

Figure 7:
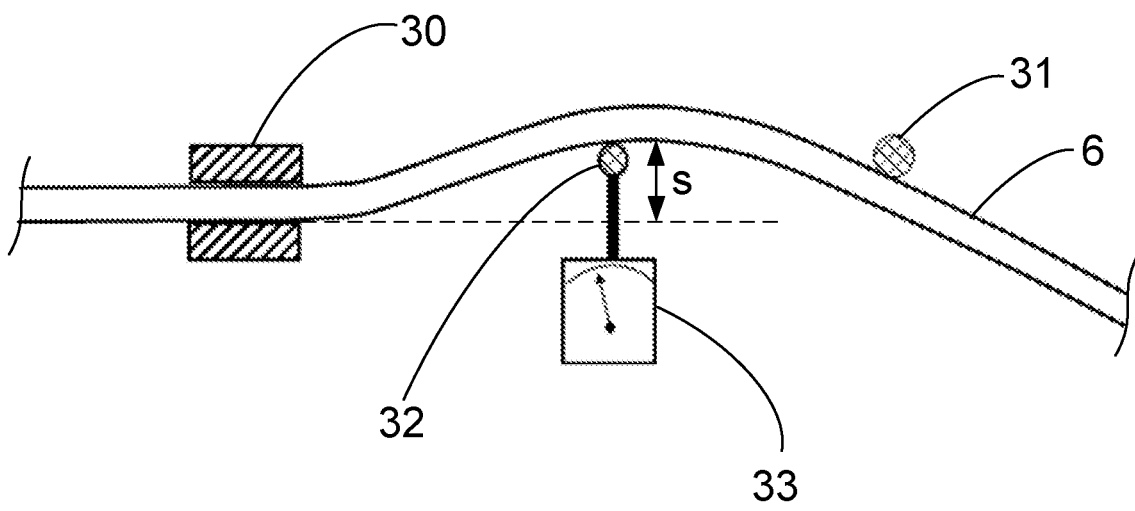
FIG. 7 shows a set-up for measuring a relative value of bending stiffness or bendability.

FIG. 7 shows a set-up for measuring a relative value for the bending stiffness or bendability. A main tube 6 is arranged in a fixture 30 providing a fixed clamping. A support roller 31 is used for limiting the movement of the main tube, while a pressure roller 32 is pressed against the main tube 6. The force necessary to bend the main tube a preselected distance s, can be used as a measure for the bendability or stiffness. This force is measured by a force meter 33. The distance s as well as the distance between fixture 30 and the support roller 31 are selected in relation to the diameter of the main tube 6. For an outer diameter of the main tube 6 in the range 10-12 mm, it has been found that a distance between fixture 30 and support roller of 150-200 mm, and a distance s in the range 10-30 mm works well. The same distances are applied when measuring at different points along the main tube 6. The distance between fixture 30 and support roller 31 will define the minimum distance from the distal end 6*b* and the proximal end 6*a*, respectively, in which it will be possible to measure.

It has been found that a main tube 6 of a colonoscope having up to approximately the double bendability towards the distal end 6*b* compared to the part at the proximal end 6*a*, often works well during an endoscopic procedure. Such a main tube 6, with twice the bendability at the most distal conditioned portion than at the unconditioned portion, has been produced using the conditioning apparatus according to the method described herein. Of course, less conditioning is also possible using the same methodology and more may be possible depending on the constitution and characteristics of the main tube, e.g. diameter and core material.

Often, the bendability at the proximal end 6*a* would be the bendability of the main tube 6 without being subjected to the conditioning process described in this disclosure. So, the main tube 6 is preferably designed to have this bendability when manufactured. The exact parameters for the conditioning process can then be defined by use of the set-up in FIG. 7, e.g., by trial-and-error testing, where the force for bending the main tube 6 the distance s in FIG. 7 is a relative measure for the bendability. In order to double the bendability, the force should be reduced to half the value.

There may be a linear change of bendability from the proximal end 6*a* the distal end. But often other functional relationships for the change in bendability are preferred. This could be more stepwise changes, or changes of a second order nature (e.g., the bendability increases with the distance from the proximal end squared). It should be noted that often only a minor part of the main tube needs the increased bendability towards the distal end. For example, for some endoscopes only 40% or less, or 30% or less, of the main tube length needs the conditioning treatment. The conditioned part of the main tube is generally located towards the distal end, preferably in the distal half of the main tube.

In relation to the temperature to be applied for the main tube 6 during the conditioning process, it has been found that heating the main tube 6 to a temperature which is at or above the Vicat softening temperature (which can be determined by the standards ASTM D1525 or ISO 306) of the polymer and which is below the melting temperature of the polymer applied, will give the best result. This temperature should at least on average be the temperature of the polymer layer at the time the temporary mechanical deformation is applied. That is to say, in the embodiment of FIGS. 5*b* and 5*c*, throughout the meander bend.

It is preferable to use a temperature below but close to the melting temperature of the polymer material, preferably above 90% or even 95% of the melting temperature, i.e. above approximately 164 degrees Celsius or above 173 degrees Celsius for a polymer material having a melting point of 182 degrees Celsius, such as Pellethane®.

However, suitable conditioning can also be achieved at lower temperatures. Even at an average temperature around half of the Vicat softening temperature for the polymer a graduated bendability can be achieved. The lower temperature may be compensated by a more intense mechanical treatment. Variables that increase the intensity of the mechanical treatment include the speed at which the treatment is applied, the bending angles, the number of bends, and the distances between the bends.

In case one or more different polymers are applied for the main tube 6, e.g. a multilayer polymer structure or a polymer blend, the temperature for the conditioning process should preferably be above the highest Vicat softening temperature, and below the lowest melting temperature, among the different polymers in the blend or multilayer polymer structure.

There will often be a temperature gradient in the polymer material 24. To reduce the risk that parts of the polymer 24 have a temperature outside of the suggested range during the conditioning process, a target temperature for the heating could be selected in the middle of this range. For the inductive heating given as example, the temperature will tend to be highest in and close to steel parts of the main tube (i.e., braiding 22 and coil 23), and lowest on the outer polymer surface. For other types of heating the temperature profile may be different.

It has been found that polymer materials of the types thermoplastic elastomer (TPE) and thermoplastic polyurethane (TPU) works well with the disclosed method. But also other polymer types can be applied. One example of polymer for the main tube is Pellethane® (a medical grade thermoplastic polyurethane elastomer) having a Vicat softening temperature of 81° C. and a melting point at 182° C.

The following items are further variations and examples of the embodiments described with reference to FIGS. 1 to 7.

1. A method for providing an insertion cord of an endoscope with graduated flexibility along the length of the insertion cord, the method comprising providing a main tube as a composite object comprising multiple layers, said multiple layers comprising at least one metal layer and a polymer material, and said main tube having a proximal and a distal end, subjecting the main tube to a conditioning process comprising application of heat and a temporary mechanical deformation along at least a part of the length of the main tube between said proximal end and said distal end, characterized in that the application of heat raises the temperature of the polymer material to a temperature above the Vicat temperature of the polymer material but below the melting point of the polymer material, and wherein the magnitude of the temporary mechanical deformation is varied along said part of the length of the main tube.

2. A method according to item 1, wherein the heat is applied to the main tube so as to increase the temperature of a sector of the main tube prior to the application of the temporary mechanical deformation of that sector.

3. A method according to item 2, wherein the temperature of the sector at the time the application of the temporary mechanical deformation is applied is above half of the Vicat temperature.

4. A method according to item 2, wherein the temperature of the sector at the time the application of the temporary mechanical deformation is applied is above the Vicat temperature.

5. A method according to item 1, where the heat is applied locally to the main tube so as to increase the temperature of a sector of the main tube during the temporary mechanical deformation of that sector.

6. A method according to any one of the preceding items, wherein the heating is adjusted to raise the average temperature of the polymer material at the temporary mechanical deformation to at least the Vicat softening temperature of the polymer material.

7. The method according to item 6, wherein the heating is adjusted to raise the average temperature of the polymer material at the temporary mechanical deformation to a temperature above the Vicat temperature but below the melting point of the polymer material.

8. The method according to item 7, wherein the heating is adjusted to raise the average temperature of the polymer material at the temporary mechanical deformation to a temperature above 90% of the melting temperature, preferably above 95% of the melting temperature of the polymer material.

9. A method according to any one of the preceding items, wherein the temporary mechanical deformation comprises a meander bend in a transverse direction of the main tube.

10. A method according to item 9, wherein the size of the meander bend in the transverse direction of the main tube increases linearly along said part of the length of the main tube from the proximal end towards the distal end of the main tube.

11. A method according to any one of the preceding items, wherein the temporary mechanical deformation comprises first meander bend in a transverse direction of the main tube and a second meander bend in the transverse direction of the main tube.

12. A method according to item 11, wherein the size of the first meander bend is less than the size of the second meander bend, wherein the second meander bend is distal of the first meander bend.

13. A method according to any one of items 9 to 12, wherein the part of the length subjected to the conditioning process is at least 15%, preferably at least 25%, and more preferably at least 35% of the length of the main tube between the proximal end and the distal end.

14. A method according to item 13, wherein the main tube part has a proximal portion extending from the handle to 50% of the length of the main tube and a distal portion extending from the proximal portion and comprising the remaining 50% of the length of the main tube, and wherein the part of the length subjected to the conditioning process is in the distal portion of the main tube.

15. A method according to any one of the preceding items, wherein the metal layer of the main tube comprises steel and the heat is applied to the steel by electro-magnetic induction.

16. A method according to any one of the preceding items, wherein a ceramic heating element is used to irradiate heat towards the main tube.

17. A method according to any one of the preceding items, wherein the main tube is subjected to the conditioning process a first time and, after the first time, a second time.

18. A method according to item 17, wherein the main tube is rotated after the first time before being subjected to the conditioning process the second time.

19. A method according to item 18, wherein the main tube is rotated, after the first time and before the second time, about an angle in the interval between 70° and 130°, preferably 90°.

20. An endoscope comprising a main tube conditioned using a process according to any one of the preceding items.

21. A method for providing an insertion cord of an endoscope with graduated flexibility along the length of the insertion cord, the method comprising: providing a main tube having a proximal end and a distal end, the main tube comprising a coil enclosed in a polymer material, and subjecting the main tube to a conditioning process comprising application of heat and a temporary mechanical deformation along at least a portion of the main tube, the temporary mechanical deformation being applied while the temperature of the polymer material of the portion of the main tube is above 50% of the Vicat temperature of the polymer material but below the melting point of the polymer material.

22. The method of item 21, wherein the temporary mechanical deformation is applied while the temperature of the polymer material of the portion of the main tube is above the Vicat temperature of the polymer material.

23. The method of items 21 and/or 22, wherein the portion of the main tube is at most 50% of a length of the main tube.

24. The method of item 23, wherein the main tube has a proximal portion extending from the handle to 50% of the length of the main tube and a distal portion extending from the proximal portion and comprising the remaining 50% of the length of the main tube, and wherein the portion of the main tube subjected to the conditioning process is in the distal portion of the main tube.

25. The method of any one of items 21-24, wherein a magnitude of the temporary mechanical deformation is varied.

26. The method of item 25, wherein the magnitude is varied continuously.

27. The method of item 25, wherein the magnitude is varied step-wise.

28. The method of any one of items 21-27, wherein the temporary mechanical deformation comprises a first bend and a first counter-bend.

29. The method of item 28, wherein the temporary mechanical deformation comprises, after the first bend and the first counter-bend, a second bend and a second counter-bend, the total amount of bending and counter-bending being complementary should that the main tube, after application of the temporary mechanical deformation, is straight.

30. The method of item 29, wherein the first bend and the first counter-bend comprise a meander bend in a transverse direction of the main tube.

31. The method of item 30, wherein the meander bend further comprises the second bend and the second counter-bend.

32. The method of items 30 or 31, wherein the size of the meander bend in the transverse direction of the main tube increases linearly from the proximal end towards the distal end of the main tube.

33. The method of item 32, wherein the portion of the main tube subjected to the conditioning process is at least 15%, preferably at least 25%, and more preferably at least 35% of the length of the main tube.

34. The method of any one of items 21-33, wherein the size of the first meander bend is less than the size of the second meander bend, wherein the second meander bend is distal of the first meander bend.

35. The method of any one of items 21-33, wherein the main tube has a proximal portion extending from the handle to 50% of the length of the main tube and a distal portion extending from the proximal portion and comprising the remaining 50% of the length of the main tube, and wherein the portion subjected to the conditioning process is in the distal portion of the main tube.

36. The method of any one of items 21-35, further comprising rotating the main tube after applying the conditioning process the first time, and subjecting the portion of the main tube to the conditioning process a second time.

37. The method of item 36, wherein rotating the main tube comprises rotating the tube about an angle in the interval between 70° and 130°, preferably about 90°.

38. The method of item 37, wherein subjecting the portion of the main tube to the conditioning process a second time comprises subjecting the portion of the main tube to the same conditioning process, albeit after rotating the main tube.

39. The method of item 37, wherein subjecting the portion of the main tube to the conditioning process a second time comprises subjecting the portion of the main tube to a different conditioning process, albeit after rotating the main tube, the different conditioning process comprising at least one of a different temperature, processing speed, and/and angle magnitude than the first conditioning process, the second conditioning process imparting a different bendability than the first conditioning process.

40. The method of any one of items 21-39, wherein the coil comprises steel and the heat is applied to the steel by electromagnetic induction.

41. The method of any one of items 21-40, wherein the main tube further comprises a braid between the coil and the polymer material.

42. The method of any one of items 21-41, wherein the polymer material comprises a co-extruded polymer structure.

43. The method of any one of items 21-41, wherein the polymer material comprises a blend of polymers.

44. The method of any one of items 21-43, wherein the heating is adjusted to raise the average temperature of the polymer material at the temporary mechanical deformation to a temperature above 90% of the melting temperature, preferably above 95% of the melting temperature of the polymer material.

45. An endoscope comprising a main tube conditioned using a process according to any one of items 21-44.

46. A system comprising a display device, and an endoscope according to items 20 or 45, the endoscope being adapted to be connected to the display device.

47. A conditioning apparatus configured to implement a method according to any one of items 1-19 and 21-44, the conditioning apparatus comprising: a heater, a sled, a first wheel, a second wheel, and a third wheel, the sled configured to translate in a longitudinal direction, the heater configured to heat a portion of a main tube to be mechanically conditioned, the main tube comprising a coil enclosed in a polymer material, the third wheel positioned between the first wheel and the second wheel and configured to translate at a non-zero angle relative to the longitudinal direction, the sled configured to pull the main tube away from the heater to cause the portion of the main tube to bend and counter-bend between the first, second and third wheels while a temperature of the portion of the main tube is above 50% of the Vicat temperature but below the melting point of the polymer material.

48. The conditioning apparatus of item 47, further comprising a linear actuator configured to translate the second wheel.

49. The conditioning apparatus of item 48, wherein the linear actuator is configured to translate the second wheel in a continuous manner.

We claim:

1. A method for providing an insertion cord of an endoscope with graduated flexibility along a length of the insertion cord, the method comprising:

provising a main tube having a proximal end and a distal end, the main tube comprising a coil enclosed in a polymer material; and subjecting the main tube to a conditioning process comprising application of heat and a temporary mechanical deformation along a portion of the main tube, the temporary mechanical deformation being applied while the polymer material of the portion of the main tube is in a softened state caused by the application of the heat but below a melting point of the polymer material.

2. The method of claim 1, wherein the temporary mechanical deformation is applied while the temperature of the polymer material of the portion of the main tube is above 81° C.

3. The method of claim 1, wherein the portion of the main tube is at most 50% of a length of the main tube.

4. The method of claim 1, wherein the temporary mechanical deformation is applied while the temperature of the polymer material of the portion of the main tube is above 81° C., wherein the main tube has a proximal portion extending from the proximal end to 50% of the length of the main tube and a distal portion extending from the proximal portion and comprising the remaining 50% of the length of the main tube, and wherein the portion of the main tube subjected to the conditioning process is in the distal portion of the main tube.

5. The method of claim 1, wherein a magnitude of the temporary mechanical deformation is varied.

6. The method of claim 1, wherein the magnitude of the temporary mechanical deformation is varied continuously.

7. The method of claim 1, wherein the portion of the main tube subjected to the conditioning process is at least 25% of the length of the main tube.

8. The method of claim 7, wherein the portion of the main tube subjected to the conditioning process is at least 35% of the length of the main tube.

9. The method of claim 1, wherein the temporary mechanical deformation comprises providing a first meander bend, the first meander bend including a first bend and a first counter-bend, the first bend and the first counter-bend being on a first plane.

10. The method of claim 9, wherein a size of the meander bend increases linearly from the proximal end towards the distal end of the main tube.

11. The method of claim 9, wherein the meander bend further comprises a second bend and a second counter-bend, the second bend and the second counter-bend being on the first plane.

12. The method of claim 11, wherein the main tube has a proximal portion extending from the handle to 50% of the length of the main tube and a distal portion extending from the proximal portion and comprising the remaining 50% of the length of the main tube, and wherein the portion subjected to the conditioning process is in the distal portion of the main tube.

13. The method of claim 9, further comprising, after providing the first meander bend, rotating the main tube and providing a second meander bend onto the portion of the main tube, the second meander bend being on a second plane different than the first plane.

14. The method of claim 13, wherein rotating the main tube comprises rotating the main tube at an angle between 70° and 130°.

15. The method of claim 13, wherein the first meander bend and the second meander bend are provided in the same manner.

16. The method of claim 1, wherein the coil comprises steel and the heat is applied to the steel by electromagnetic induction.

17. The method of claim 1, wherein the main tube further comprises a braid between the coil and the polymer material.

18. The method claim 1, wherein the heat applied to raise an average temperature of the polymer material to a temperature above 90% of the melting temperature of the polymer material.

* * * * *